(12) United States Patent
Larsson

(10) Patent No.: US 6,856,822 B2
(45) Date of Patent: Feb. 15, 2005

(54) MULTI-ELECTRODE CATHETER

(75) Inventor: Åke Larsson, Jäfälla (SE)

(73) Assignee: Maquet Critical Care AB, Solna (SE)

( * ) Notice: Subject to any disclaimer, the term of this patent is extended or adjusted under 35 U.S.C. 154(b) by 0 days.

(21) Appl. No.: 10/654,056

(22) Filed: Sep. 3, 2003

(65) Prior Publication Data
US 2004/0077936 A1 Apr. 22, 2004

(30) Foreign Application Priority Data
Oct. 22, 2002 (SE) ................................. 0203108

(51) Int. Cl.$^7$ ................................. A61B 5/04
(52) U.S. Cl. ................. 600/373; 600/374; 600/380; 600/393
(58) Field of Search ................ 600/373, 374, 600/380, 381, 393

(56) References Cited

U.S. PATENT DOCUMENTS

| 5,303,704 A | * | 4/1994 | Molacek et al. ............ 600/377 |
| 5,591,142 A | | 1/1997 | Van Erp |
| 5,820,560 A | | 10/1998 | Sinderby et al. |
| 6,024,693 A | | 2/2000 | Schock et al. |
| 6,259,938 B1 | | 7/2001 | Zarychta et al. |
| 2003/0199949 A1 | * | 10/2003 | Pardo ........................ 607/117 |

FOREIGN PATENT DOCUMENTS

| EP | 1 145 731 | 10/2001 |
| WO | WO 91/17785 | 11/1991 |
| WO | WO 98/51370 | 11/1998 |
| WO | WO 0003637 | 1/2000 |

* cited by examiner

*Primary Examiner*—Beverly M. Flanagan
(74) *Attorney, Agent, or Firm*—Schiff Hardin LLP

(57) ABSTRACT

A multi-electrode catheter has a longitudinally extending body with a number of longitudinally extending lumens formed therein and a number of electrode assemblies. Each assembly has an electrode located at an external surface of a caudal section of the body and an electrical conductive surface extending longitudinally within an associated lumen of the number of lumens connected to a cephalad section of the body. The conductive electrical surface forms at least a portion of an internal wall of the associated lumen and is in electrical connection with a different one of the electrodes forming the electrode assemblies.

5 Claims, 2 Drawing Sheets

MULTI-ELECTRODE CATHETER

BACKGROUND OF THE INVENTION

1. Field of the Invention

The present invention relates to a multi-electrode catheter and in particular to a multi-electrode measurement catheter for measuring esophageal or diaphragmal electromyographic (EMG) signals.

2. Description of the Prior Art

It is known from, for example, U.S. Pat. Nos. 5,820,560 and 6,259,938 to provide a multi-electrode EMG measurement catheter that has a flexible, longitudinally extending, body for insertion into the esophagus of a patient and a number of externally mounted electrodes. The electrodes are located at longitudinally spaced-apart positions at a caudal section of the body in order to receive, in use, diaphragmal EMG signals. A corresponding number of electrical conductors in the form of insulated wires are provided and these are located within a lumen of the body. Each wire is connected to an associated different one of the external electrodes and runs within the same lumen from the associated electrode to a cephalad section of the body where an external connection to an EMG signal processing system may be established.

SUMMARY OF THE INVENTION

It is an object of the present invention to provide a multi-electrode catheter, which is less complicated, and therefore easier to manufacture, than conventional multi-electrode catheters of the type described above.

This object is achieved in accordance with the principles of the present invention in a multi-electrode catheter having a longitudinally extending body with a number of longitudinally extending lumens formed therein, and a number of electrode assemblies. Each electrode assembly has an electrode located at an external surface of a caudal section of the body and an electrically conductive surface extending longitudinally within an associated lumen, connected to a cephalad section of the body. The conductive electrical surface forms at least a portion of an internal wall of the associated lumen, so that the conductive surface on the interior wall of each lumen is electrically connected to a different one of the electrodes.

By forming at least one lumen with at least a portion of the internal wall section having a conductive section which extends from the region of the electrode to the cephalad section, a less complicated, and therefore easier to manufacture, catheter is achieved.

By providing a number of lumens, each with at least a section of an internal wall having a conductive surface in electrical connection to an associated single electrode of the multiple electrode assemblies, an electrical connection between each electrode and the cephalad section of the catheter can be relatively easily established.

DESCRIPTION OF THE PREFERRED EMBODIMENTS

Figure 1:
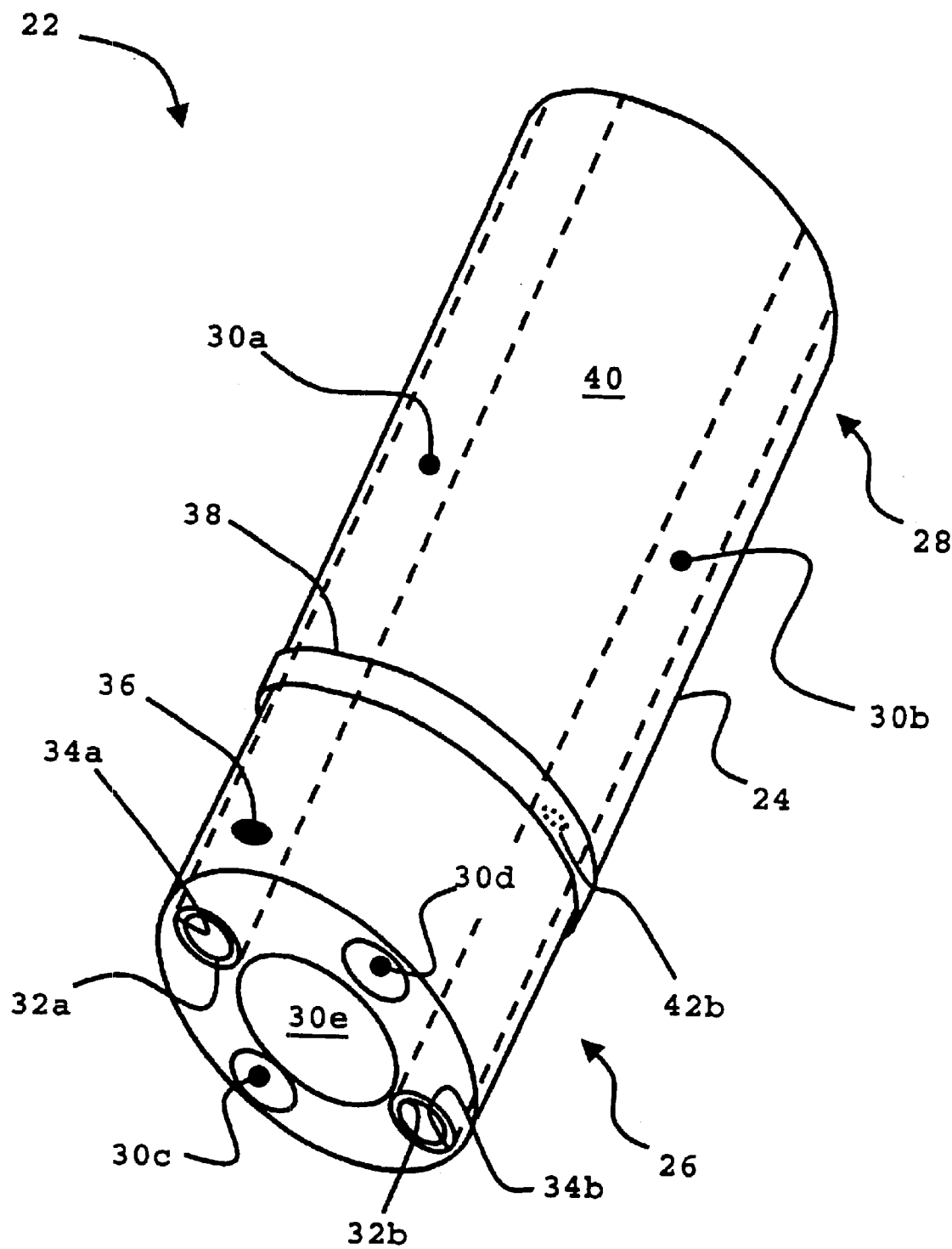
FIG. 1 is a schematic illustration of a first embodiment of a catheter according to the present invention.
Figure 2A:
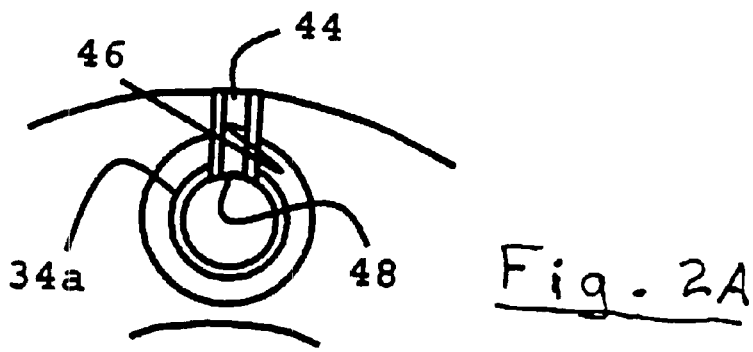
FIG. 2A illustrates a point contact arrangement as an alternative to that shown in FIG. 2.
Figure 2:
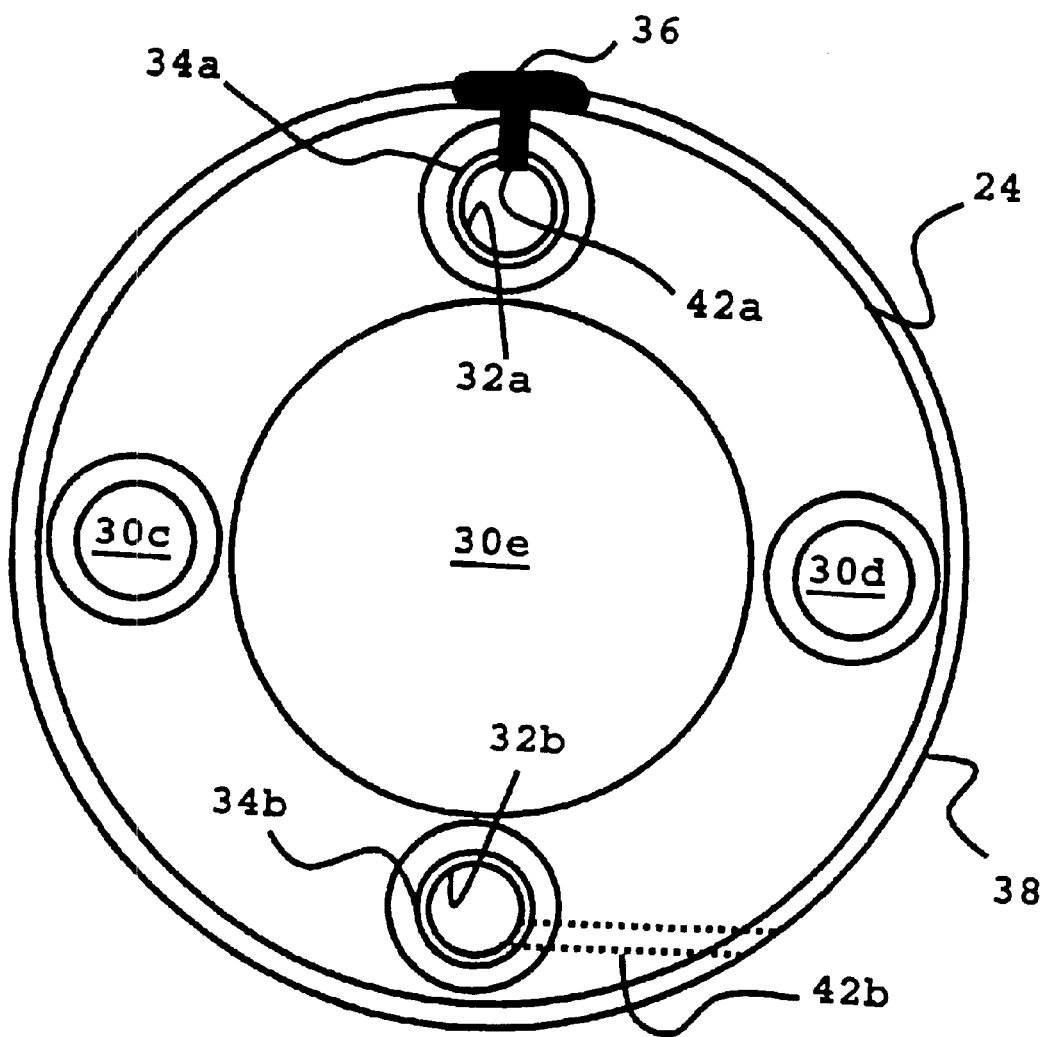
FIG. 2 is a schematic sectional view of the catheter of FIG. 1.

As shown in FIG. 1 and FIG. 2, a catheter 22 has a longitudinally extending body 24 having a caudal section 26 and a cephalad section 28. As with known catheter arrangements this body 24 is formed from, for example, polyurethane and is provided with a number of longitudinally extending lumens 30a–30e. In the present embodiment only two of the lumens 30a and 30b are each provided with an electrically conducting surface 32a and 32b that, in the present example, entirely covers an inner wall 34a or 34b of the corresponding lumen 30a and 30b. Each conductive surface 32a and 32b extends from the caudal section 26 to the cephalad section 28 of the catheter 22 so as to be substantially longitudinally co-extensive with the associated lumen 30a and 30b.

A number of electrode assemblies, being no more in number than (here the same as) the number of lumens 30a and 30b having conducting surfaces 32a and 32b, is also provided as part of the catheter 2. Each assembly has an electrode 36 or 38 located on an external surface 40 of the caudal section 26 of the body 24, and an associated electrical contact 42a or 42b, that extends from the external surface 40 to a one of the conducting surfaces 32a or 32b of an associated lumen 30a or 30b to provide an electrically conducive path between its associated electrode 36 or 38 and the conducting surface 32a or 32b that now forms the electrical conductor of the assembly.

As can be seen from the sectional view of the catheter 22 through the electrode 36, that is shown in FIG. 2, the embodiment provides a first electrode assembly with a point electrode 36, formed integrally with an associated contact 42a which extends through the body 24 of the catheter 2 to contact its associated electrical conductor, the surface 32a, of the lumen 30a. An alternative point electrode arrangement is illustrated in FIG. 2A that depicts the lumen 30a. A hole 44, preferably with electrically conducting inner walls 46, connects the external surface 40 with the conducting surface 32a, a portion 48 of which surface 32a also terminates the hole 44 to seal against ingress of fluid into the lumen 30a from external the catheter 22. In this manner the hole 44 and the terminating portion 48 of the conducting surface 32a effectively forms a point electrode.

There is also provided in the present embodiment a second electrode assembly comprising ring electrode 38 in electrical connection with its associated contact 42b which extends through the body 24 of the catheter 2 to contact its associated electrical conductor, the surface 32b, of the lumen 30b. The ring electrode 38 may be formed in a manner well known in the art, for example, by a physically separate metallic ring located about the outer surface 40 of the catheter 22, or by an integral conductive trace, formed, for example using sputtering or other deposition techniques.

It will be appreciated that the catheter according to the present invention may be provided with more electrode assemblies of similar construction and that some or all of the electrodes 36, 38, 44 and 48 of the plurality of assemblies may be identical.

Although modifications and changes may be suggested by those skilled in the art, it is the intention of the inventor to embody within the patent warranted hereon all changes and modifications as reasonably and properly come within the scope of his contribution to the art.

I claim as my invention:

1. A multi-electrode catheter comprising:

a longitudinally extending body adapted for insertion in a subject, said body having a caudal section and a cephalad section and a plurality of lumens formed therein proceeding between said caudal section and said cephalad section, each of said lumens having an internal wall, said caudal section having an external surface and said body having a body portion disposed between said internal wall and said external surface;

a plurality of electrode assemblies respectively including a plurality of electrodes located at said external surface of the caudal section of the body;

at least some of said lumens having an electrically conductive surface formed on the internal wall thereof; and a plurality of electrical connections proceeding through said body portion and respectively electrically connecting the electrically conductive surface of at least some of said lumens to different ones of said electrodes.

2. A multi-electrode catheter as claimed in claim 1, wherein at least one of said electrical connections comprises a through-hole in said body portion internally plated with electrically conductive material.

3. A multi-electrode catheter as claimed in claim 1 wherein at least one of said electrical connections comprises a solid plug comprised of electrically conductive material proceeding through an opening in said body portion.

4. A multi-electrode catheter as claimed in claim 1 wherein at least one of said electrode assemblies is an electrode dot.

5. A multi-electrode catheter as claimed in claim 1 wherein at least one of said electrode assemblies is an electrode ring.

* * * * *